(12) United States Patent
Nakagawa et al.

(10) Patent No.: US 9,820,370 B2
(45) Date of Patent: Nov. 14, 2017

(54) HEAT TRANSFER SYSTEM FOR AN INDUCTIVELY COUPLED PLASMA DEVICE

(71) Applicant: Hitachi High-Tech Science Corporation, Minato-ku, Tokyo (JP)

(72) Inventors: Yoshitomo Nakagawa, Tokyo (JP); Yutaka Ikku, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 0 days.

(21) Appl. No.: 15/066,345

(22) Filed: Mar. 10, 2016

(65) Prior Publication Data

US 2016/0270201 A1 Sep. 15, 2016

(30) Foreign Application Priority Data

Mar. 10, 2015 (JP) .................. 2015-047700

(51) Int. Cl.
*H05H 1/30* (2006.01)
*H01J 49/10* (2006.01)

(52) U.S. Cl.
CPC .............. *H05H 1/30* (2013.01); *H01J 49/105* (2013.01)

(58) Field of Classification Search
CPC ................................ H01J 49/105; H05H 1/28
See application file for complete search history.

(56) References Cited

U.S. PATENT DOCUMENTS

| | | | | |
|---|---|---|---|---|
| 3,296,410 A * | 1/1967 | Hedger | .................. | H05H 1/30 219/121.36 |
| RE29,304 E * | 7/1977 | Greenfield | ............ | G01N 21/73 219/121.36 |
| 4,582,121 A * | 4/1986 | Casey | .................... | F28D 15/02 122/33 |
| 4,849,675 A * | 7/1989 | Muller | .................... | H01J 27/16 313/230 |
| 5,086,255 A * | 2/1992 | Okamoto | ................. | H05H 1/46 250/288 |
| 5,194,731 A * | 3/1993 | Turner | .................. | G01N 21/73 250/281 |
| 5,383,019 A * | 1/1995 | Farrell | .................. | G01N 21/73 219/121.54 |
| 5,877,471 A * | 3/1999 | Huhn | ...................... | H05H 1/30 219/121.43 |
| 6,693,253 B2 * | 2/2004 | Boulos | .................... | H05H 1/30 219/121.47 |

(Continued)

FOREIGN PATENT DOCUMENTS

JP H05-050649 U 7/1993
JP H08-203692 A 8/1996

*Primary Examiner* — Brooke Purinton
(74) *Attorney, Agent, or Firm* — Banner & Witcoff, Ltd.

(57) ABSTRACT

An inductively coupled plasma generating device is configured to include a plasma torch, a high frequency induction coil and a high frequency power source. In addition, a heat transfer member, in which a first terminal is connected to the high frequency induction coil and a second terminal is connected to a cooling block, is disposed in the inductively coupled plasma generating device. The second terminal of the heat transfer member is located above the first terminal, thereby causing condensed operating fluid to fall and move toward the first terminal due to the action of gravity. Accordingly, it is possible to achieve excellent cooling capacity by improving circulation and mobility of the operating fluid.

3 Claims, 7 Drawing Sheets

(56) References Cited

U.S. PATENT DOCUMENTS

2004/0045497 A1\* 3/2004 Kriews .................... G01N 1/04
  117/2
2012/0120604 A1\* 5/2012 Hao ...................... H01L 23/427
  361/701

\* cited by examiner

CONNECTING POSITION FOR
HEAT TRANSFER MEMBER

GROUND SIDE

FIG.6B

CONNECTING POSITION FOR
HEAT TRANSFER MEMBER

GROUND SIDE

HEAT TRANSFER SYSTEM FOR AN INDUCTIVELY COUPLED PLASMA DEVICE

CROSS-REFERENCE TO RELATED APPLICATIONS

This application claims priority from Japanese Patent Application No. 2015-047700 filed on Mar. 10, 2015, the entire subject-matter of which is incorporated herein by reference.

TECHNICAL FIELD

The disclosure relates to an inductively coupled plasma generating device which uses inductively coupled plasma (ICP) so as to excite or ionize an element. The disclosure particularly relates to cooling of a high frequency induction coil which supplies high frequency power in order to generate the inductively coupled plasma. In addition, the disclosure relates to an inductively coupled plasma analysis device which excites or ionizes the element of an analysis target sample by using the inductively coupled plasma generating device so as to obtain an atomic emission line.

BACKGROUND

As a material of a high frequency induction coil serving as a medium for supplying energy to plasma, silver or copper which has low electric resistivity is used. However, the electric resistivity is not zero. Consequently, heat of approximately 10 W to 100 W is generated in the high frequency induction coil. A calorific value depends on a high frequency power value or a surface state (oxidized state or the like) of the high frequency induction coil. As a method of preventing the resistivity of the high frequency induction coil from being changed or impaired due to the heat generation, a cooling method of circulating water (JP-UM-A-H05-50649) is known. That is, the high frequency induction coil has a structure in which a pipe is wound around a plasma torch so that cooling water flows into the pipe. Here, the cooling water is subjected to circulation and heat exchange by using a cooling water circulating device belonging to an inductively coupled plasma device. In addition, a method is also known which cools the induction coil by blowing air from the outside, circulating gas in the pipe, or using a heat pipe (JP-A-H08-203692).

Figure 7A:
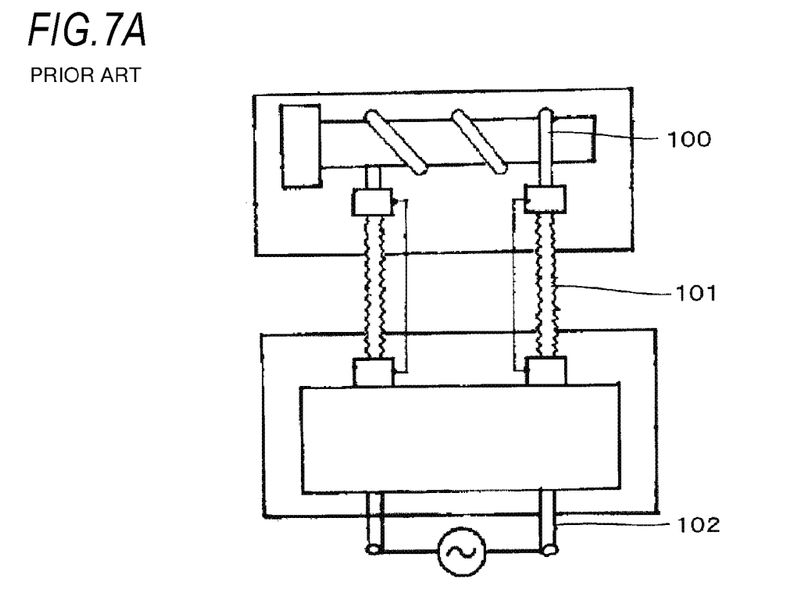

As illustrated in FIG. 7A, JP-UM-A-H05-50649 discloses an inductively coupled plasma mass spectrometer which can miniaturize a drive mechanism for moving a high frequency induction coil 100, and in which cooling water is caused to circulate in the high frequency induction coil 100 via a flexible pipe 101 and a pipeline 102.

Figure 7B:
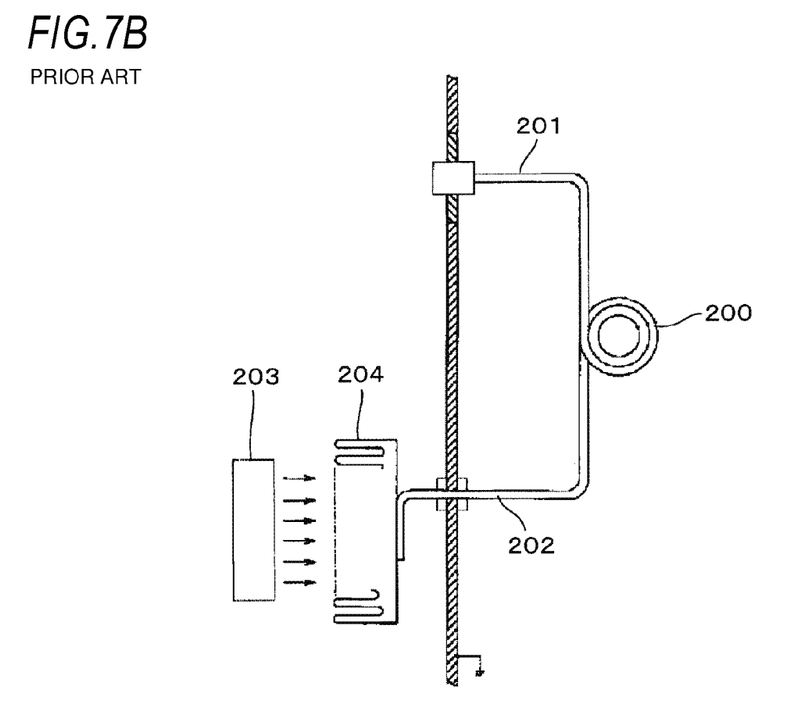

As illustrated in FIG. 7B, JP-A-H08-203692 discloses an inductively coupled plasma generating device which can prevent a temperature increase of an output coil (high frequency induction coil) 200, since the output coil 200 is configured to include a heat pipe, a high frequency application terminal 201 functions as an evaporator, a ground terminal 202 functions as a condenser, a heat sink 204 is cooled by a fan 203, and heat generated by the output coil 200 is efficiently transferred to the heat sink 204 through the output coil 200 so as to be discharged to the air.

When the cooling water disclosed in JP-UM-A-H05-50649 is used, the following problems arise. The cooling water circulating device has heat exchanging efficiency of approximately 50%, and a pump for circulating the cooling water consumes energy. That is, the cooling water is cooled by consuming energy more than heat energy generated in the high frequency induction coil, thereby causing environmental burdens. Since the cooling water circulating device is additionally installed, the cost increases. In addition, when the cooling water is used, maintenance work for a cooling water system is needed in order to avoid accidents resulting from water leaks or clogged pipelines. Consequently, the maintenance work inevitably requires labor and cost.

In addition, when the high frequency induction coil is cooled by gas instead of the water, cooling capacity is inferior to that in water cooling. Thus, the high frequency induction coil is operated in a state where the temperature is higher than that in the water cooling. For this reason, a surface of the high frequency induction coil is progressively oxidized. Then, electric resistance of the high frequency induction coil varies with the lapse of time, and the power of plasma varies with the lapse of time, even if a high frequency output of the inductively coupled plasma generating device remains unchanged. That is, even when analysis conditions of the inductively coupled plasma analysis device are not changed, there is a problem in that the power of the plasma varies with the lapse of time and the analysis capability also varies.

The high frequency induction coil itself disclosed in JP-A-H08-203692 is the heat pipe. However, JP-A-H08-203692 does not disclose a specific configuration of the heat pipe except that the heat pipe is disposed horizontally, and does not consider liquid circulating efficiency. In addition, an evaporator of the heat pipe is disposed in an output coil terminal rather than a coil section which becomes hottest in the high frequency induction coil. Consequently, there is a problem in that cooling efficiency becomes poor without utilizing characteristics of the heat pipe. Then, in order to radiate the heat generated in a high frequency induction coil, it is indispensable to install a cooling fan for cooling a condenser. The cooling fan is operated to radiate the heat, thereby causing environmental burdens. Therefore, there is a problem in that the cooling fan results in an increased cost of the inductively coupled plasma analysis device.

SUMMARY

Illustrative aspects of the disclosure provide an inductively coupled plasma generating device which can cool a high frequency induction coil with excellent cooling capacity without using cooling water, and an inductively coupled plasma analysis device which employs the inductively coupled plasma generating device.

An inductively coupled plasma generating device according to one illustrative aspect of the disclosure is an inductively coupled plasma generating device configured to obtain an atomic emission line by using inductively coupled plasma so as to excite or ionize an element, the inductively coupled plasma generating device comprising: a plasma torch to which carrier gas containing a target element is guided; a high frequency induction coil wound around the plasma torch; a heat transfer member having a first terminal and a second terminal, the first terminal being connected to the high frequency induction coil; and a cooling block connected to the second terminal of the heat transfer member, wherein operating fluid is enclosed in the heat transfer member, the operating fluid being evaporated through the first terminal by heat generated by the high frequency induction coil to form steam, the steam of the operating fluid moving toward the second terminal so as to move the heat generated by the high frequency induction coil toward the second terminal, and the steam being condensed at the second terminal so that the condensed operating fluid moves toward the first terminal, and wherein the second terminal is at a position at least above the first terminal.

In one illustrative aspect of the inductively coupled plasma generating device, the heat transfer member may be configured by a heat pipe in which the operating fluid is enclosed.

In one illustrative aspect of the inductively coupled plasma generating device, the cooling block may be connected to an exhaust duct chimney that is disposed above the plasma torch.

In one illustrative aspect of the inductively coupled plasma generating device, the cooling block may be connected to an axial input block which is disposed in an axial direction of inductively coupled plasma.

In one illustrative aspect of the inductively coupled plasma generating device, at least a portion including a ground side terminal of the high frequency induction coil may be configured by the heat transfer member.

In another illustrative aspect of the disclosure, there may be provided an inductively coupled plasma emission spectrometric analyzer comprising the inductively coupled plasma generating device according to any one of the above-described illustrative aspects.

In still another illustrative aspect of the disclosure, there may be provided an inductively coupled plasma mass spectrometer comprising the inductively coupled plasma generating device according to any one of the above-described illustrative aspects.

According to the disclosure, a high frequency induction coil is cooled without using cooling water. Therefore, environmental burdens are reduced, the cost for installing a cooling water circulating device is no longer required, and maintenance work for a cooling water system is also no longer required. In addition, cooling capacity is improved compared to that in gas cooling in the related art. Thus, constant power of plasma can be maintained, and analysis capability does not vary. Then, a second terminal of a heat transfer member is arranged at a position above a first terminal, thereby causing condensed operating fluid to fall and move toward the first terminal due to the action of gravity. Accordingly, circulation and mobility of the operating fluid is improved. Therefore, it is possible to provide an inductively coupled plasma generating device which has excellent heat radiating performance.

BRIEF DESCRIPTION OF THE DRAWINGS

FIGS. 6A and 6B are circuit diagrams illustrating a position for connecting the heat transfer member when viewed from an electric circuit including a high frequency induction coil according to the disclosure, in which FIG. 6A illustrates Example 1, and FIG. 6B illustrates Example 2; and FIGS. 7A and 7B are schematic views illustrating each configuration of inductively coupled plasma generating devices in the related art, in which FIG. 7A illustrates JP-UM-A-H05-50649, and FIG. 7B illustrates JP-A-H08-203692.

DETAILED DESCRIPTION

Hereinafter, preferred embodiments of an inductively coupled plasma generating device (ICP generating device) according to the disclosure will be described in detail with reference to FIGS. 1 and 3 to 6, by citing an example of an inductively coupled plasma emission spectrometric analyzer functioning as one type of inductively coupled plasma analysis device. However, as illustrated in FIG. 2, the inductively coupled plasma generating device according to the disclosure is also applicable to an inductively coupled plasma mass spectrometer which is another type of the inductively coupled plasma analysis device.

Figure 1:
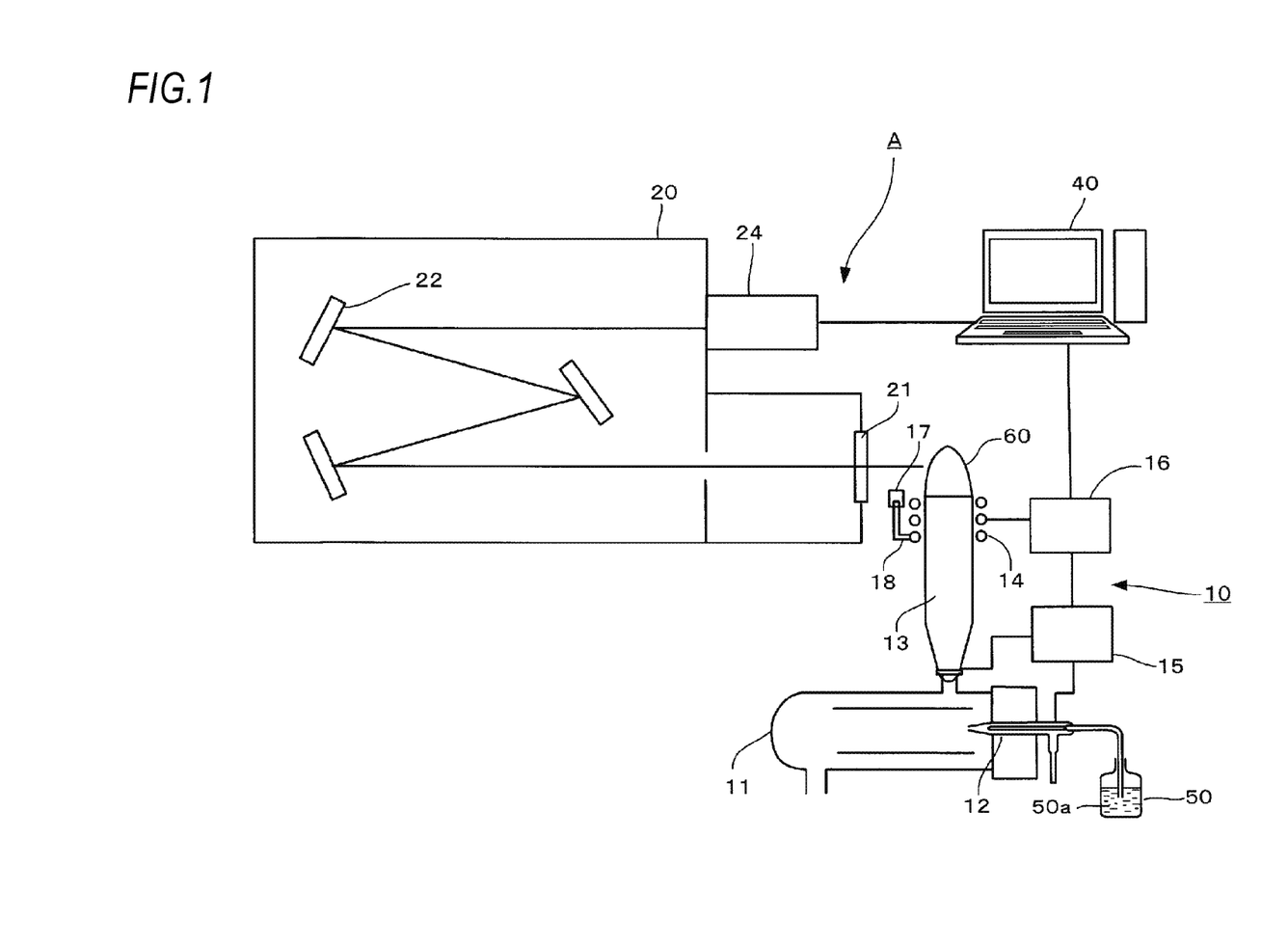
FIG. 1 is a conceptual diagram illustrating an example of an ICP emission spectrometric analyzer according to the disclosure.
Figure 2:
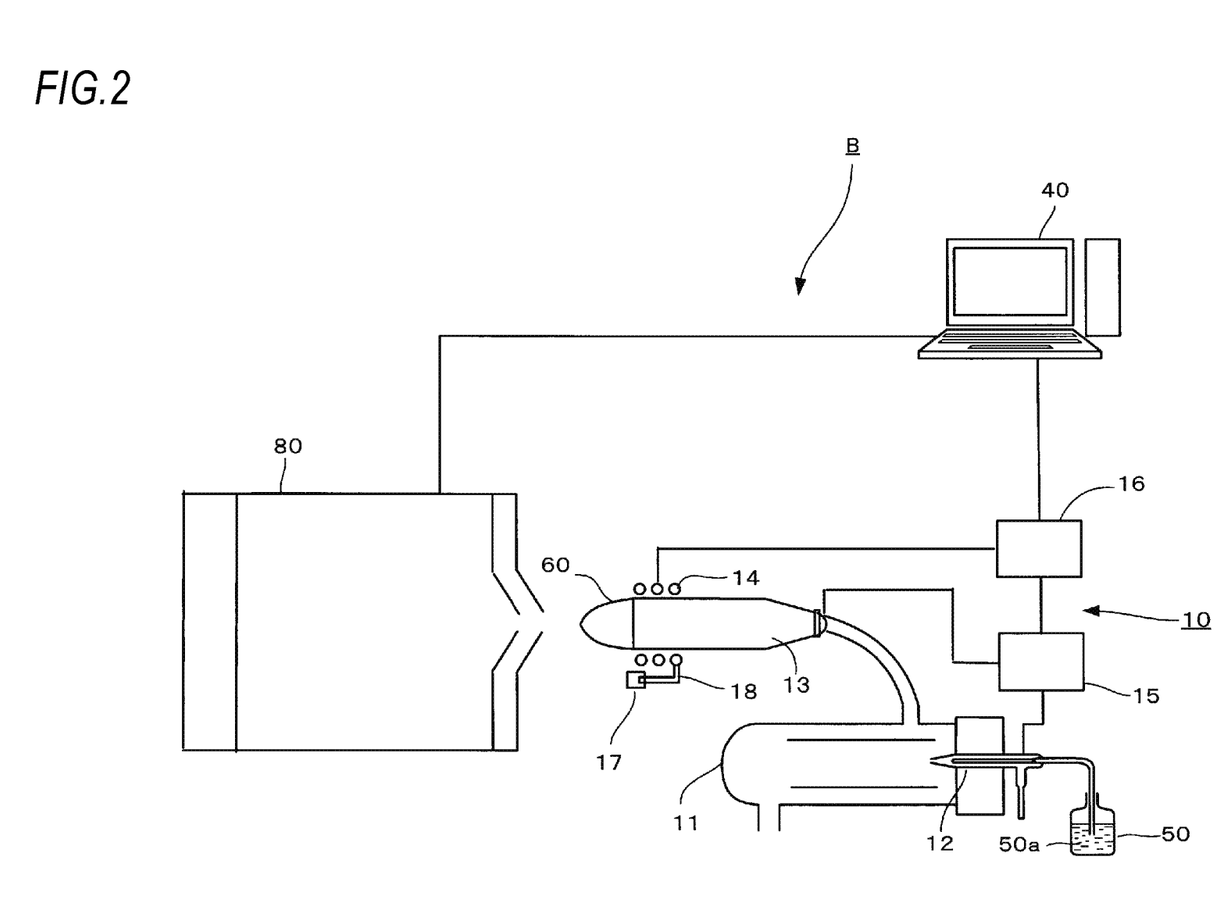
FIG. 2 is a conceptual diagram illustrating an example of an ICP mass spectrometer according to the disclosure.

FIG. 1 is a conceptual diagram illustrating an example of the ICP emission spectrometric analyzer according to the disclosure.

An inductively coupled plasma generating device 10 is incorporated into an inductively coupled plasma (ICP) emission spectrometric analyzer A. The ICP emission spectrometric analyzer A includes a spectroscope 20 and a control unit 40 in addition to the inductively coupled plasma generating device 10.

The inductively coupled plasma generating device 10 is schematically configured to include a plasma torch 13, a high frequency induction coil 14, and a high frequency power source 16. In addition, a heat transfer member 18 in which one terminal thereof (first terminal) is connected to the high frequency induction coil 14 and the other terminal (second terminal) is connected to a cooling block 17 is disposed in the inductively coupled plasma generating device 10.

The spectroscope 20 includes an input window 21, an optical component 22 such as a lens, a diffraction grating, and a mirror, and a detector 24.

The control unit 40 is a computer, and controls the overall ICP emission spectrometric analyzer A. In accordance with a wavelength of emitted light of a detection target atomic emission line, the control unit 40 controls the spectroscope 20 so as to measure an emission intensity profile or to measure emission peak intensity and background intensity of a target wavelength.

Carrier gas (argon gas) supplied into a nebulizer 12 is ejected from a tip of the nebulizer 12 into a spray chamber 11 at a speed of 0.8 L/min, for example. A suction force generated by negative pressure of the carrier gas causes an analysis target solution sample 50a in a sample container 50 to be picked up and ejected from the tip of the nebulizer 12. The ejected solution sample 50a is allowed to have uniform particles and stable air flows inside the spray chamber 11, and is guided to the plasma torch 13 having a cylindrical pipe structure. A gas control unit 15 controls a flow rate or pressure of the carrier gas to be supplied to the nebulizer 12 or gas (plasma gas, auxiliary gas, or chamber gas) to be supplied to the plasma torch 13.

Then, a high frequency current is caused to flow into the high frequency induction coil 14 from the high frequency power source 16, a sample molecule (or atom) of the solution sample 50a is heated and excited so as to emit light, and inductively coupled plasma 60 (hereinafter, referred to as plasma) is generated above the plasma torch 13. A frequency of the high frequency current is generally 27.12 MHz or 40 MHz, and high frequency power is approximately 500 W to 2,000 W.

An atomic emission line obtained by the plasma 60 exciting or ionizing an analysis target element of the solution sample 50a enters the inside of the spectroscope 20 through the input window 21. The atomic emission line is spectrally dispersed by the optical component 22 inside the spectroscope 20, and is detected by the detector 24. The atomic emission line spectrally dispersed and detected in the spectroscope 20 is analyzed by means of data processing in the control unit 40. The control unit 40 performs qualitative analysts on the element (for example, a trace impurity element) contained in the solution sample 50a, based on the wavelength of the atomic emission line (spectral line), and performs quantitative analysis on the element, based on the intensity of the atomic emission line (spectral line).

FIG. 2 is a conceptual diagram illustrating an example of an inductively coupled plasma mass spectrometer (ICP mass spectrometer) B according to the disclosure. The inductively coupled plasma generating device according to the disclosure is also applicable to the ICY mass spectrometer B which includes a mass spectrometer (mass measuring device) 80.

Figure 3:
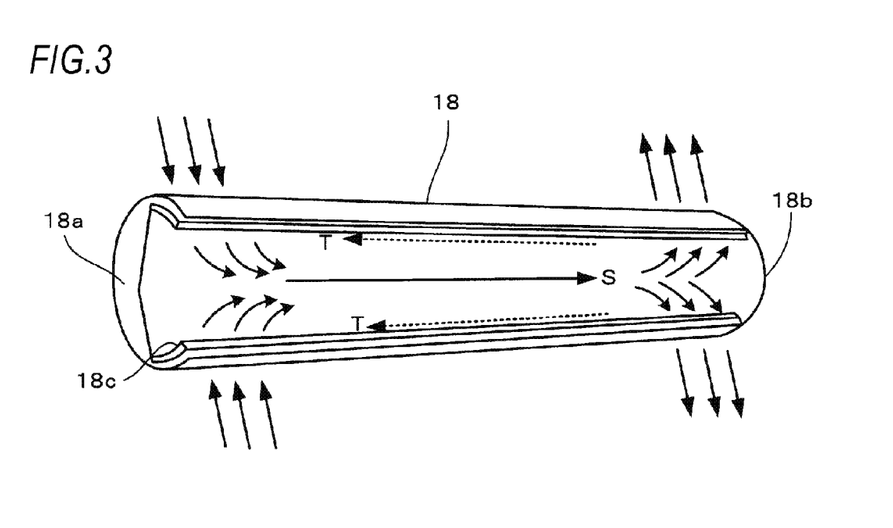
FIG. 3 is a schematic view illustrating a schematic configuration of a heat pipe enclosing operating fluid which is an example of a heat transfer member according to the disclosure.

FIG. 3 is a schematic view illustrating a schematic configuration of a heat pipe enclosing operating fluid which is an example of the heat transfer member 18.

For example, the heat pipe configuring the heat transfer member 18 is a made from metal and a substantially cylindrical sealed container in which a first terminal 18a and a second terminal 18b are enclosed. Operating fluid is maintained at a reduced pressure and enclosed inside the container, and an inner wall of the heat pipe includes a wick (capillary structure) 18c for recirculating the operating fluid. The operating fluid is evaporated in the first terminal 18a due to external heat, steam moves to a low temperature portion of the second terminal 18b (refer to an arrow S in the drawing), and the steam moving toward the second terminal 18b is condensed. The steam returns to the operating fluid, and moves toward the first terminal 18a through the wick 18c (refer to an arrow T in the drawing). A steam pressure difference between the first terminal (evaporator) 18a and the second terminal (condenser) 18b causes the operating fluid to move fast from the first terminal 18a toward the second terminal 18b. The vaporized operating fluid is cooled and liquefied in the second terminal 18b. A capillary force of the wick 18c causes the operating fluid to quickly move toward the first terminal 18a. This process is repeatedly performed. The operating fluid may be moved from the second terminal 18b toward the first terminal 18a by utilizing gravity. In the drawing, a linear heat pipe is illustrated. However, the heat pipe may be freely bent or curved by means of bending work. A shape of the heat pipe is not particularly limited.

Figure 4:
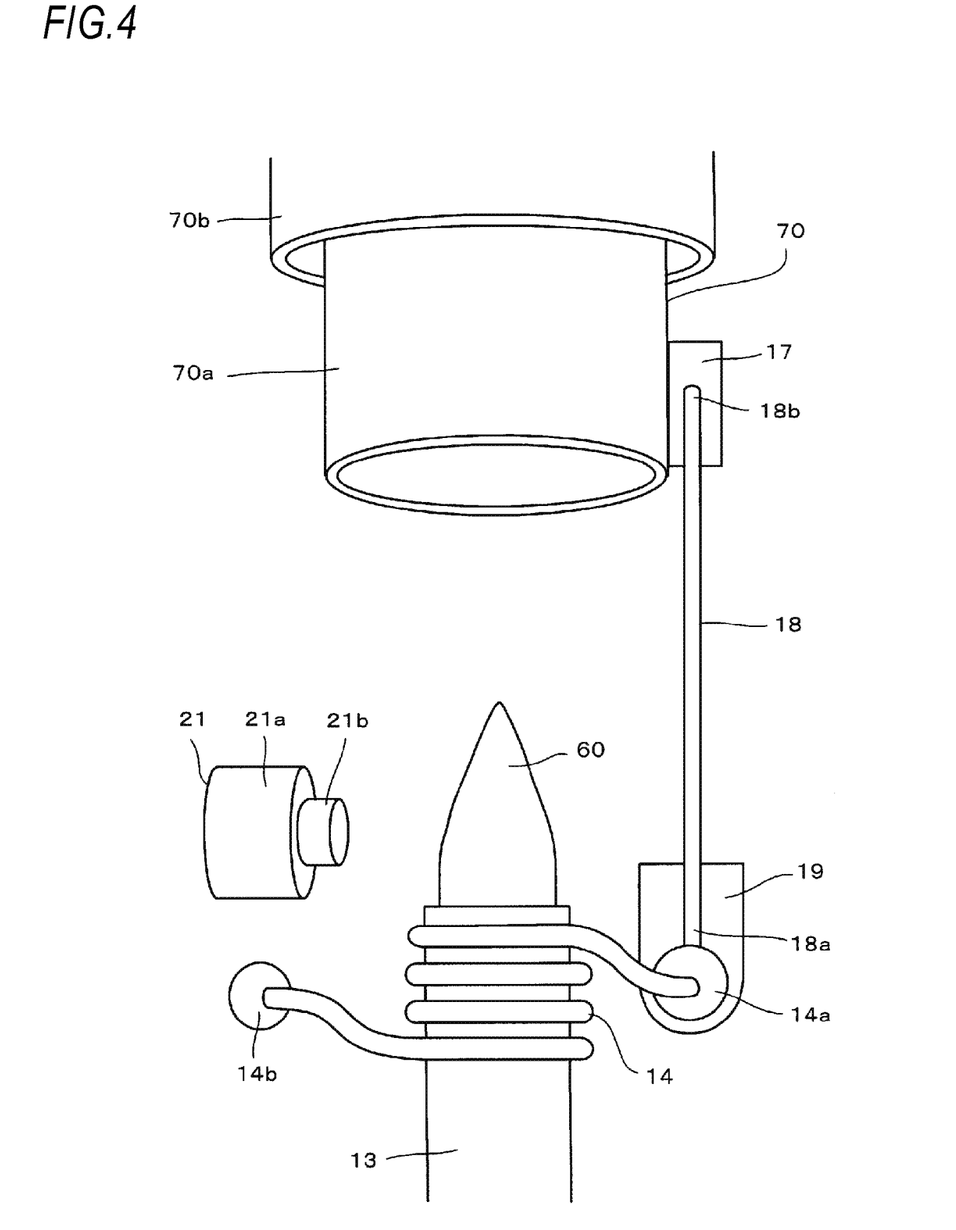
FIG. 4 is a conceptual diagram illustrating an example of a first embodiment of an inductively coupled plasma generating device according to the disclosure.

FIG. 4 is a conceptual diagram illustrating an example of a first embodiment of the inductively coupled plasma generating device 10.

A substantially cylindrical exhaust duct chimney 70 is arranged above the plasma torch 13 of the inductively coupled plasma generating device 10. According to the present embodiment, the exhaust duct chimney 70 has an inner cylinder 70a and an outer cylinder 70b. Heat generated in the plasma 60 or a reaction product of the solution sample 50a is exhausted through a duct. An exhaust amount of the exhaust duct chimney 70 is approximately 1 $m^3$/min to 10 $m^3$/min.

The input window 21 of the spectroscope 20 which has a horizontal input block 21a and a horizontal observation window 21b is arranged beside the plasma torch 13. Light generated in the plasma 60 passes through the horizontal input block 21a, and is detected after being subjected to wavelength demultiplexing in the spectroscope 20. A target element of the analysis target solution sample 50a is identified, based on the emission wavelength, and the concentration is determined, based on the emission intensity.

The high frequency induction coil 14 in which one terminal has a ground side terminal 14a, and the other terminal has a hot side terminal 14b to which a high frequency voltage is applied is wound around the plasma torch 13 of the inductively coupled plasma generating device 10. In addition, the ground side terminal 14a is connected to a heat contact block 19, and the heat contact block 19 is connected to the first terminal 18a, of the heat transfer member 18. The second terminal 18b is arranged above the first terminal 18a, and the second terminal 18b is connected to the cooling block 17 which is connected to the inner cylinder 70a of the exhaust duct chimney 70.

As a material of the high frequency induction coil 14, silver or copper which has low electric resistivity is used. However, the electric resistivity is not zero. Consequently, heat of approximately 10 W to 100 W is generated in the high frequency induction coil 14. Therefore, as described above, the heat of the high frequency induction coil 14 is moved toward the cooling block 17 by using the heat transfer member 18, thereby cooling the high frequency induction coil 14.

According to the first embodiment, the evaporator which is the first terminal 18a of the heat transfer member 18 and the ground side terminal 14a of the high frequency induction coil 14 are connected to each other. Furthermore, the ground side terminal 14a and the heat contact block 19 are thermally connected to each other. In addition, the condenser which is the second terminal 18b of the heat transfer member 18 is thermally connected to the inner cylinder 70a of the exhaust duct chimney 70 via the cooling block 17.

Heat conductivity of the heat transfer member 18 is approximately 1,000 times that of silver. Since the heat conductivity is very high, the heat of the high frequency induction coil 14 quickly moves toward the inner cylinder 70a of the exhaust duct chimney 70. Since duct exhaust air is blown into the exhaust duct chimney 70, the inner cylinder 70a of the exhaust duct chimney 70 functions as a heat radiating plate. Then, the heat of the high frequency induction coil 14 is radiated and exhausted through the duct.

In order to structurally improve the heat conductivity of the heat transfer member 18, it is preferable to adopt a configuration in which the first terminal 18a is located below and the second terminal 18b is located above. According to the present embodiment, the heat is moved from the high frequency induction coil 14 located below to the exhaust duct chimney 70 located above, thereby improving the heat conductivity. The heat of the high frequency induction coil 14 can be reliably radiated, and the high frequency induction coil 14 can be cooled with excellent cooling capacity.

In addition, the heat transfer member 18 is connected to the ground side terminal 14a of the high frequency induction coil 14. Accordingly, the heat transfer member 18 and the exhaust duct chimney 70 serve as a ground potential. Therefore, stable analysis can be performed while high frequency noise is not generated due to both of these or an inductively coupled state between the high frequency induction coil 14 and the plasma 60 is not disturbed. Then, the heat conductivity of the heat transfer member 18 greatly depends on arrangements or configurations for a heat input and a heat output. Accordingly, it is possible to obtain excellent heat conductivity by adopting a correct arrangement (configuration).

In the first embodiment, a case has been described where the cooling block 17 is connected to the inner cylinder 70a of the exhaust duct chimney 70. However, the cooling block 17 may be connected to the outer cylinder 70b, or the exhaust duct chimney 70 may serve as the cooling block 17.

Figure 5:
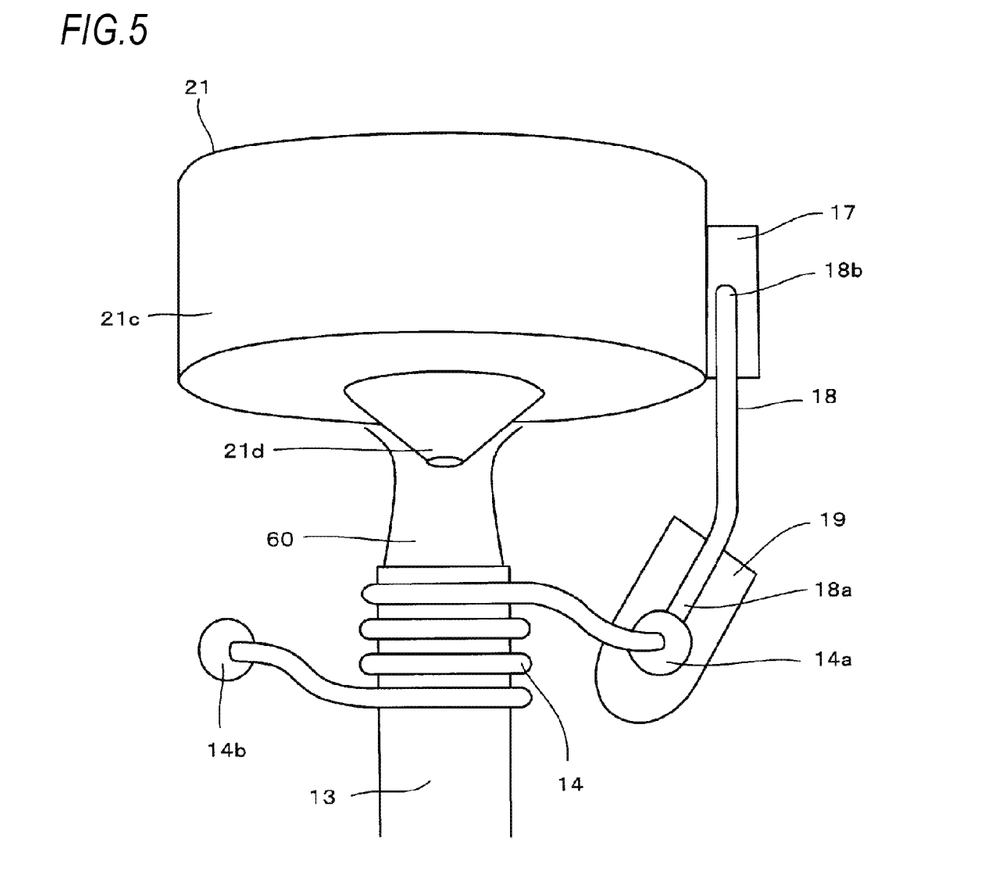
FIG. 5 is a conceptual diagram illustrating an example of a second embodiment of the inductively coupled plasma generating device according to the disclosure.

FIG. 5 is a conceptual diagram illustrating an example of a second embodiment of the inductively coupled plasma generating device 10.

The input window 21 of the spectroscope 20 which has an axial input block 21c and an axial observation window 21d is arranged above the plasma torch 13 of the inductively coupled plasma generating device 10. The high frequency induction coil 14 in which one terminal has the ground side terminal 14a and the other terminal has the hot side terminal 14b is wound around the plasma torch 13. In addition, the ground side terminal 14a is connected to the heat contact block 19, and the heat contact block 19 is connected to the first terminal 18a of the heat transfer member 18. The second terminal 18b is arranged above the first terminal 18a, and the second terminal 18b is connected to the cooling block 17 which is connected to the axial input block 21c of the input window 21.

According to the second embodiment, light emission of the plasma 60 is observed in the axial direction (perpendicular direction). That is, the axial input block 21c is arranged in the axial direction of the plasma 60 which is parallel to the light emitting direction of the plasma 60. Light is introduced to the axial input block 21c from the axial observation window 21d, and is detected after being subjected to wavelength demultiplexing in the spectroscope 20. A target element of the analysis target solution sample 50a is identified, based on the emission wavelength, and the concentration is determined, based on the emission intensity.

In addition, according to the second embodiment, the evaporator which is the first terminal 18a of the heat transfer member 18 and the ground side terminal 14a of the high frequency induction coil 14 are connected to each other. The heat contact block 19 reliably brings the first terminal 18a and the high frequency induction coil 14 into thermal contact with each other. In addition, the second terminal 18b of the heat transfer member 18 comes into thermal contact with the axial input block 21c via the cooling block 17.

Heat conductivity of the heat transfer member 18 is approximately 1,000 times that of silver. Since the heat conductivity is very high, the heat of the high frequency induction coil 14 quickly moves toward the axial input block 21c. Since the axial input block 21c is heated up by the plasma 60, the axial input block 21c is initially cooled by using water. Then, the heat of the high frequency induction coil 14 is radiated in conjunction with the cooling of the axial input block 21c. In this manner, the heat of the high frequency induction coil 14 can be exhausted without a need to install a cooling water circulation system for the high frequency induction coil 14.

In FIG. 5, the input window 21 of the spectroscope 20 which has the axial input block 21c and the axial observation window 21d is arranged above the plasma torch. However, the arrangement is not limited thereto. For example, the plasma torch may be tilted by an angle of 90 degrees, and the input window 21d of the spectroscope 20 which has the axial input block 21c and the axial observation window 21 may be arranged in the axial direction of the plasma generated from the plasma torch.

In order to structurally improve the heat conductivity of the heat transfer member 18, it is preferable to adopt a configuration in which the first terminal 18a is located below and the second terminal 18b is located above. According to the present embodiment, the heat is moved from the high frequency induction coil 14 located below toward the axial input block 21c located above, thereby improving the heat conductivity. The heat of the high frequency induction coil 14 can be reliably radiated, and the high frequency induction coil 14 can be cooled with excellent cooling capacity.

In addition, the heat transfer member 18 is connected to the ground side terminal 14a of the high frequency induction coil 14. Accordingly, the heat transfer member 18 and the axial input block 21c serve as a ground potential. Therefore, stable analysis can be performed while high frequency noise is not generated due to both of these or an inductively coupled state between the high frequency induction coil 14 and the plasma 60 is not disturbed. Then, the heat conductivity of the heat transfer member 18 greatly depends on arrangements or configurations for a heat input and a heat output. Accordingly, it is possible to obtain excellent heat conductivity by adopting a correct arrangement (configuration).

In the second embodiment, a case has been described where the cooling block 17 is connected to the axial input block 21c of the input window 21. However, as long as the heat generated in the high frequency induction coil 14 can be radiated, the cooling block 17 may be connected to other portions of the input window 21. The axial input block 21c or the input window 21 may be the cooling block 17.

According to the first embodiment and the second embodiment, the first terminal 18a which is the evaporator of the heat transfer member 18 is brought into thermal contact with the ground side terminal 14a of the high frequency induction coil 14. Here, if a configuration is adopted in which the first terminal 18a of the heat transfer member 18 serves as a portion or an entire portion including the ground side terminal 14a of the high frequency induction coil 14, the high frequency induction coil 14 can be more efficiently cooled.

Figure 6A:
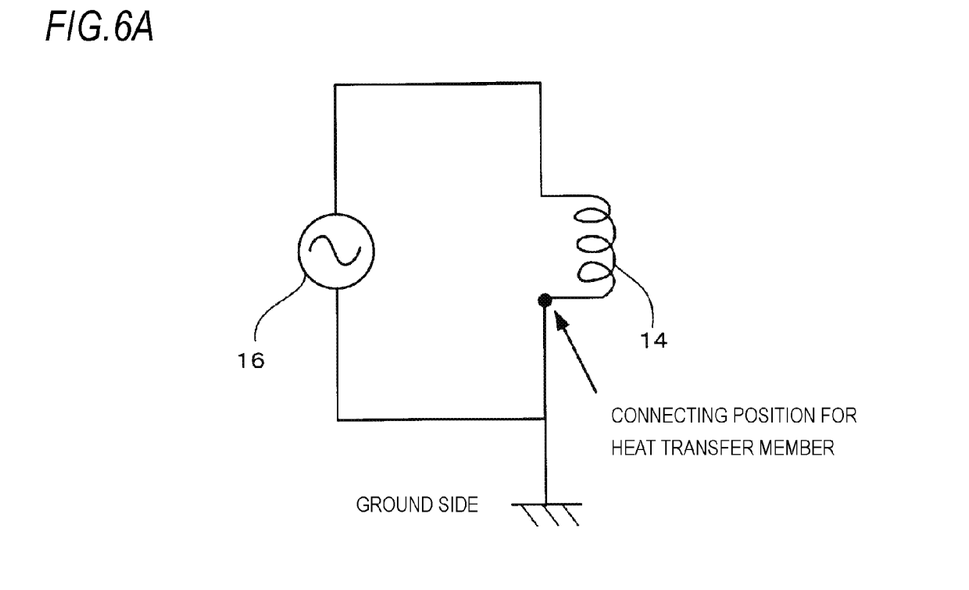
Figure 6B:
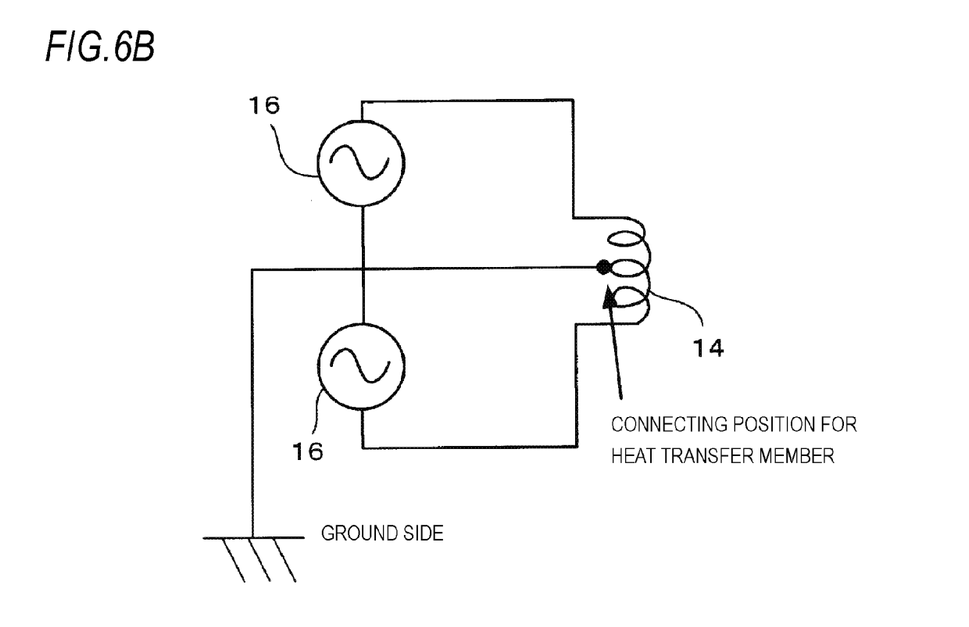

FIGS. 6A and 6B are circuit diagrams illustrating a position for connecting the heat transfer member 18 when viewed from an electric circuit including the high frequency induction coil 14. FIG. 6A illustrates Example 1, and FIG. 6B illustrates Example 2.

In FIG. 6A, one terminal of the high frequency induction coil 14 is grounded. In Example 1, the first terminal 18a of the heat transfer member 18 is brought into contact with a ground side of the high frequency induction coil 14. In this manner, the cooling block 17 from the heat transfer member 18 can serve as aground potential.

In FIG. 6B, a halfway point of the high frequency induction coil 14 is grounded. Then, a high frequency whose phase is changed with respect to aground position by an angle of 180° is applied to both terminals of the high frequency induction coil 14. In Example 2, the first terminal 18a of the heat transfer member 18 is brought into contact with the ground potential position of the halfway point of the high frequency induction coil 14. In this manner, the cooling block 17 from the heat transfer member 18 can serve as aground potential.

Without being limited to the above-described embodiments, the disclosure can be appropriately modified or improved. In addition, as long as the present invention can be achieved, materials, shapes, dimensions, numerical values, forms, the number, and arrangement locations of the respective configuration elements in the above-described embodiments may be optionally employed, and do not limit the present invention.

An inductively coupled plasma generating device according to the disclosure is applicable to various uses in efficiently cooling a high frequency induction coil.

What is claimed is:

1. An inductively coupled plasma analysis device configured to obtain an atomic emission line by using inductively coupled plasma so as to excite or ionize an element, the inductively coupled plasma analysis device comprising:
   a plasma torch to which carrier gas containing a target element is guided, the plasma torch including an opening from which plasma is generated;
   a high frequency induction coil wound around the plasma torch;
   a horizontal input block or an axial input block configured to receive a part of light of the plasma generated in the plasma torch;
   a spectroscope configured to detect the light having passed through the horizontal input block or the axial input block;
   a heat transfer member having a first terminal and a second terminal, the first terminal being connected to the high frequency induction coil; and
   a cooling block connected to the second terminal of the heat transfer member,
   wherein operating fluid is enclosed in the heat transfer member, the operating fluid being evaporated through the first terminal by heat generated by the high frequency induction coil to form steam, the steam of the operating fluid moving toward the second terminal so as to move the heat generated by the high frequency induction coil toward the second terminal, and the steam being condensed at the second terminal so that the condensed operating fluid moves toward the first terminal,
   wherein at least one of an exhaust duct chimney and the axial input block is disposed above the plasma torch such that the at least one of the exhaust duct chimney and the axial input block overlaps the opening of the plasma torch in a vertical direction, the exhaust duct chimney configured to exhaust heat of the plasma generated in the plasma torch and/or a reaction product, and
   wherein the cooling block is connected to the at least one of the exhaust duct chimney and the axial input block.

2. The inductively coupled plasma analysis device according to claim 1, wherein the heat transfer member comprises a heat pipe in which the operating fluid is enclosed.

3. The inductively coupled plasma analysis device according to claim 1, wherein the cooling block directly contacts the at least one of the exhaust duct chimney and the axial input block.

* * * * *